United States Patent [19]
Wright

[11] 4,008,231
[45] Feb. 15, 1977

[54] PREPARATION OF 3-METHOXYMETHYLCEPHALOSPORINS
[75] Inventor: Ian G. Wright, Greenwood, Ind.
[73] Assignee: Eli Lilly and Company, Indianapolis, Ind.
[22] Filed: Sept. 15, 1975
[21] Appl. No.: 613,388
[52] U.S. Cl. .......................................... 260/243 C
[51] Int. Cl.$^2$ ............. C07D 501/26; C07D 501/28; C07D 501/30
[58] Field of Search ................................ 260/243 C
[56] References Cited
UNITED STATES PATENTS 3,665,003  5/1972  Kennedy et al. ............... 260/243 C Primary Examiner—Nicholas S. Rizzo
Assistant Examiner—Diana G. Rivers
Attorney, Agent, or Firm—William C. Martens, Jr.; Everet F. Smith

[57] ABSTRACT

A 3-methoxymethylcephalosporin acid is prepared by reacting a 3-hydroxymethylcephalosporin acid with a reagent selected from the group consisting of trifluoroacetic anhydride, phosphorus trichloride, phosphorus oxychloride, and thionyl chloride, and reacting the resulting intermediate with methanol.

9 Claims, No Drawings

PREPARATION OF 3-METHOXYMETHYLCEPHALOSPORINS

BACKGROUND AND SUMMARY OF THE INVENTION

This invention relates to a process for preparing cephalosporin compounds, and particularly, free acid 3-methoxymethylcephalosporins.

3-Methoxymethylcephalosporins are recognized in the literature. However, a facile and convenient method affording substantial product conversion from readily available starting materials has to date not been available. It is to such a method that this invention is directed.

U.S. Pat. Nos. 3,658,799 and 3,665,003 each describe the conversion of a 3-hydroxymethylcephalosporin to its corresponding 3-alkoxymethylcephalosporin.

One of the methods described in U.S. Pat. No. 3,665,003 involves the use of diazomethane. This method has certain deficiencies. First, an ester protecting group is employed, and this necessitates two additional steps in the preparative sequence, one to incorporate the protecting group and the other to effect its removal. Secondly, diazomethane is both highly toxic and explosive. Its use therefore tends to be greatly limited.

Another method described in U.S. Pat. Nos. 3,658,799 and 3,665,003 involves the use of an activated derivative of an acid HX having a pKa of not more than 4.0 in combination with a 3-hydroxymethylcephalosporin. The resulting 3—XCH$_2$ cephalosporin compound then is reacted with an alcohol or phenol to obtain the desired 3-etherified hydroxymethyl compound. In this regard, the acid which is employed is a haloacetic acid, specifically and preferably dichloroacetic acid. This method also has a distinct drawback. It too requires the use of a cephalosporin having a protected 4-carboxy group. Failure to suitably protect the 4-carboxy group prior to conversion of the 3-hydroxymethylcephalosporin using a haloacetic acid such as is described in these patents results in formation of substantial quantities of the undesired lactone with little or no formation of the desired 3-methoxymethylcephalosporin. Again, therefore, it is essential in the haloacetic acid process described in these two patents to include the step of blocking the carboxyl group of the cephalosporin starting material at the outset and declocking it upon completion of the reaction.

This invention overcomes these prior art deficiencies and thus is directed to a process for preparing in substantial yield a free acid 3-methoxymethylcephalosporin from its corresponding free acid 3-hydroxymethylcephalosporin. The costly and time-consuming steps of blocking the carboxyl group of the cephalosporin reactant and deblocking that of the product are avoided by the discovery which constitutes the basis of this invention.

Thus, this invention is directed to a process for preparing a 3-methoxymethylcephalosporin of the formula

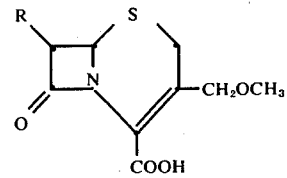

in which R is an acylamino or an imido group which comprises contacting a compound of the formula

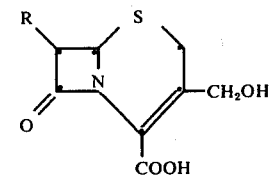

with at least four equivalents of an activating agent selected from the group consisting of trifluoroacetic anhydride, phosphorus trichloride, phosphorus oxychloride, and thionyl chloride at a temperature of from about −30° C. to about +20° to produce an intermediate compound, separating the resulting intermediate from excess activating agent by treating the reaction mixture at reduced pressure and at a temperature not in excess of about 50° C., and reacting said intermediate with an excess of methanol at a temperature of from about 45° to about 75° C. to produce the aforementioned product.

DETAILED DESCRIPTION OF THE INVENTION

As indicated hereinabove, this invention is directed to a process for preparing a free acid 3-methoxymethylcephalosporin from the corresponding free acid 3-hydroxymethylcephalosporin. It involves the use of reagents and conditions of reaction specifically selected to avoid excessive lactone formation, which formation is recognized to readily occur when one applies prior art methods to a cephalosporin which has not been suitably protected at the 4-carboxy function.

The compounds which are employed as starting materials in the process of this invention can be any of a wide variety of 7-acylamino- or 7-imidocephalosporins. The identity of the particular acylamino or imido group in the 7-position is not crucial to the ongoing of the reaction. Preferably, the group will be one which is inert to the conditions of reaction employed in the process of this invention. However, even if the substituent in the 7-position should contain a moiety which may be reactive under the conditions of reaction of the process of this invention, this will not materially affect the ongoing of the process defined by this invention, although it may alter the identity of the group present in the 7-position of the final product from that which was present in the starting material. Therefore, a wide variety of 7-substituents can be employed. As noted, however, it is highly preferred that the particular substituent in the 7-position be one which does not contain a function which will be reactive to the reagents and under the conditions employed in the process of this invention.

Typical of the 7-acylamino and 7-imido groups of the 3-hydroxymethylcephalosporin starting materials used in the process of this invention and herein defined by the term R include the following:

1. an imido group of the formula

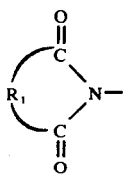

in which $R_1$ is $C_2$–$C_4$ alkylene or 1,2-phenylene;

2. an amido group of the formula

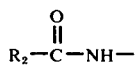

in which $R_2$ is a. hydrogen, $C_1$–$C_3$ alkyl, halomethyl, 4-amino-4-carboxybutyl, 4-protected amino-4-protected carboxybutyl, benzyloxy, 4-nitrobenzyloxy, t-butyloxy, 2,2,2-trichloroethoxy, 4-methoxybenzyloxy, 3-(2-chlorophenyl)-5-methylisoxazol-4-yl;

b. the group R' in which R' is 1,4-cyclohexadienyl, phenyl, or phenyl substituted with one or two halogens, hydroxy, protected hydroxy, nitro, cyano, trifluoromethyl, $C_1$–$C_4$ alkyl, or $C_1$–$C_4$ alkoxy;

c. a group of the formula R'—(O)$_m$—CH$_2$— in which R' is as defined above and m is 0 or 1;

d. a group of the formula

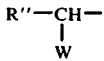

in which R'' is R' as defined above, 2-thienyl, or 3-thienyl, and W is hydroxy, protected hydroxy, carboxy, protected carboxy, amino, or protected amino;

e. a group of the formula R'''—CH$_2$— in which R''' is 2-thienyl, 3-thienyl, 2-furyl, 3-furyl, 2-thiazolyl, 5-tetrazolyl, 1-tetrazolyl, or 4-isoxazolyl; or R is 3. an imidazolidinyl group of the formula

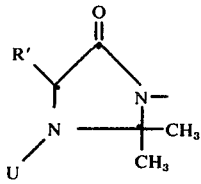

in which R' is as defined above and U is nitroso or acetyl.

As indicated hereinabove, the 7-amido function of the 3-hydroxymethylcephalosporins used in the process of this invention preferably has the formula

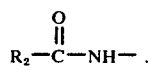

Specific illustrations of the group $R_2$ include, for example, hydrogen, methyl, ethyl, n-propyl, isopropyl, chloromethyl, bromomethyl, 4-amino-4-carboxybutyl, 4-acetamido-4-p-nitrobenzyloxycarbonylbutyl, benzyloxy, 4-nitrobenzyloxy, t-butyloxy, 2,2,2-trichloroethoxy, 4-methoxybenzyloxy, 1,4-cyclohexadienyl, phenyl, 2-chlorophenyl, 3,4-dichlorophenyl, 3-chloro-4-fluorophenyl, 4-hydroxyphenyl, 3-formyloxyphenyl, 4-nitrophenyl, 2-cyanophenyl, 4-trifluoromethylphenyl, 3-methylphenyl, 2-ethylphenyl, 4-n-propylphenyl, 4-t-butylphenyl, 2-methoxyphenyl, 4-ethoxyphenyl, 3-isopropyloxyphenyl, 4-isobutyloxyphenyl, 1,4-cyclohexadienylmethyl, benzyl, 3-bromobenzyl, 2,5-dichlorobenzyl, 3-hydroxybenzyl, 4-chloroacetoxybenzyl, 2-nitrobenzyl, 3-cyanobenzyl, 4-trifluoromethylbenzyl, 3-methylbenzyl, 4-n-butylbenzyl, 2-methoxybenzyl, 3-isopropoxybenzyl, 1,4-cyclohexadienyloxymethyl, phenoxymethyl, 3-iodophenoxymethyl, 4-fluorophenoxymethyl, 3-benzyloxyphenoxymethyl, 4-benzyhydryloxyphenoxymethyl, 4-hydroxyphenoxymethyl, 3-trityloxyphenoxymethyl, 4-nitrobenzyloxyphenoxymethyl, 4-trimethylsilyloxyphenoxymethyl, 3-nitrophenoxymethyl, 4-cyanophenoxymethyl, 2-trifluoromethylphenoxymethyl, 3-methylphenoxymethyl, 4-n-propylphenoxymethyl, 4-n-butylphenoxymethyl, 3-methoxyphenoxymethyl, 4-ethoxyphenoxymethyl, α-(hydroxy)-thien-2-ylmethyl, α-(benzhydryloxy)-thien-2-ylmethyl, α-(4-nitrobenzyloxycarbonyl)-thien-2-ylmethyl, α-(carboxy)-thien-2-ylmethyl, α-(t-butyloxycarbonylamino)-thien-2-ylmethyl, α-(amino)-thien-2-ylmethyl, α-(formyloxy)-thien-3-ylmethyl, α-(benzyloxycarbonyl)-thien-3-ylmethyl, α-(benzyloxycarbonylamino)-thien-3-ylmethyl, α-(chloroacetoxy)-1,4-cyclohexadienylmethyl, α-(t-butyloxycarbonyl)-1,4-cyclohexadienylmethyl, α-4-nitrobenzyloxycarbonylamino)-1,4-cyclohexadienylmethyl, α-hydroxybenzyl, α-trityloxybenzyl, α-(4-methoxybenzyloxy)-benzyl, α-(t-butyloxycarbonylamino)-benzyl, α-(2,2,2-trichloroethoxycarbonylamino)benzyl, α-carboxybenzyl, α-(trimethylisilyloxy)-4-bromobenzyl, α-(benzhydryloxycarbonyl)-3-chlorobenzyl, α-aminobenzyl, α-(trimethylsilylamino)-4-fluorobenzyl, α,4-di(formyloxy)-benzyl, α-(4-nitrobenzyloxycarbonyl)-3-chloroacetoxybenzyl, α-(4-methoxybenzyloxycarbonylamino)-4-benzhydryloxybenzyl, α-benzyloxy-3-nitrobenzyl, α-(4-nitrobenzyloxycarbonyl)-2-cyanobenzyl, α-(t-butoxycarbonylamino)-4-trifluoromethylbenzyl, α-formyloxy-4-methylbenzyl, α-benzyloxycarbonyl -3-n-butylbenzyl, α-benzyloxycarbonylamino-4-methoxybenzyl, α-formyloxy- 3-isopropoxybenzyl, thien-2-ylmethyl, thien-3-ylmethyl, fur-2-ylmethyl, fur-3-ylmethyl, thiazol-2-ylmethyl, tetrazol-5-ylmethyl, tetrazol-1-ylmethyl, isoxazol-4-ylmethyl, 3-(2-chlorophenyl)-5-methylisoxazol-4-yl, and the like.

Of the above it is highly preferred that $R_2$ be hydrogen, methyl, 4-nitrobenzyloxy, benzyl, phenoxymethyl, thien-2-ylmethyl, tetrazol-1-ylmethyl, or α-(t-butyloxycarbonylamino)benzyl.

In portions of the definition provided herein for the group $R_2$, the terms "protected amino", "protected hydroxy", and "protected carboxy" are employed.

The term "protected amino", when employed herein, refers to an amino group substituted with one of the commonly employed amino blocking groups such as t-butyloxycarbonyl, benzyloxycarbonly, 4-methoxybenzyloxycarbonyl, 4-nitrobenzyloxycarbonyl, 2,2,2-trichloroethoxycarbonyl, 1-carbomethoxy-2-propenyl formed with methyl acetoacetate, trimethylsilyl, and the like. Additional typical amino protecting groups are described by J. W. Barton in *Protective Groups in Organic Chemistry*, J. F. W. McOmie, Ed., Plenum Press, New York, N. Y., 1973, Chapter 2. Any of these are recognized as useful within the meaning of the term "protected amino" employed herein.

The term "protected hydroxy", when employed herein, refers to the readily cleavable groups formed with an hydroxyl group such as a formyloxy group, a chloroacetoxy group, a benzyloxy group, a benzhydryloxy group, a trityloxy group, a 4-nitrobenzyloxy group, a trimethylsilyloxy group, and the like. Other hydroxy protecting groups, including those described by C. B. Reese in *Protecting Groups in Organic Chemistry*, supra, Chapter 3, are considered to be within the term "protected hydroxy" as used herein.

The term "protected carboxy", when employed herein, refers to a carboxy group which has been protected by one of the commonly used carboxylic acid protecting groups employed to block or protect the carboxylic acid functionality of a compound while a reaction or sequence of reactions involving other functional sites of the compound are carried out. Such protected carboxy groups are noted for their ease of cleavage to the corresponding carboxylic acid by hydrolytic or by hydrogenolytic methods. Examples of carboxylic acid protecting groups include t-butyl, benzyl, 4-methoxybenzyl, $C_2$–$C_6$ alkanoyloxymethyl, 2-iodoethyl, 4-nitrobenzyl, diphenylmethyl (benzhydryl), phenacyl, p-halophenacyl, dimethylallyl, 2,2,2-trichloroethyl, succinimidomethyl and like ester forming moieties. The nature of such ester forming groups is not critical as long as the ester formed therewith is stable under the reaction conditions of the process of this invention. Furthermore, other known carboxy protecting groups such as those described by E. Haslam in *Protective Groups in Organic Chemistry*, supra, Chapter 5, are considered to be within the term "protected carboxy" as used herein.

Preferred groups within the term "protected carboxy" are tert-butyl, 4-methoxybenzyl, 4-nitrobenzyl, benzhydryl, and 2,2,2-trichloroethyl.

In the foregoing definitions, hydroxy, amino, and carboxy protecting groups, of course, are not exhaustively described. The function of these groups is to protect reactive functional groups during preparation of a desired product. They then are removed without disruption of the remainder of the molecule. Many such protecting groups are well known in the art, and their use is equally applicable in the process of this invention.

The 7-substituent of the 3-hydroxymethylcephalosporin used in the process of this invention also can be an imido group, preferably a cyclic imido group of the formula

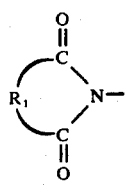

This cyclic imido group, defined by $R_1$ taken together with the nitrogen-carbonyl combination to which it is bonded, can be formed by reacting the 7-amino group of a 7-aminocephalosporin with a dicarboxylic acid or anhydride or other reactive variant thereof, followed by reacting the resulting derivative with a $C_1$ to $C_4$ alkyl haloformate, for example, ethyl chloroformate, in the presence of an organic base. $R_1$ is $C_2$–$C_4$ alkylene or 1,2-phenylene and can be considered as being the residue of a dicarboxylic acid, the cyclic imide thus represented being prepared from such dicarboxylic acid, its anhydride or an appropriate reactive variant thereof. Cyclic imides can be prepared, for example, from acids such as malonic, succinic, adipic, glutaric, phthalic, and the like, or their respective anhydrides, as well as relates compounds and compounds of similar reactivities. Additional examples of cyclic anhydrides of the type defined are found in the prior art such as in the *Journal of Organic Chemistry*, Volume 26, pp. 3365–3367 (September, 1961).

In addition, the group R in the process of this invention can be an imidazolidinyl group of the formula

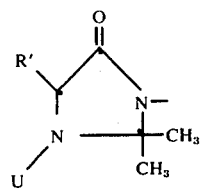

in which U is nitroso or acetyl and R' is 1,4-cyclohexadienyl, phenyl, or phenyl substituted with 1 or 2 halogens, hydroxy, protected hydroxy, nitro, cyano, trifluoromethyl, $C_1$–$C_4$ alkyl, or $C_1$–$C_4$ alkoxy.

The group thus represented is a 2,2-dimethyl-3-nitroso-5-oxo-4-(substituted)-imidazolidin-1-yl group or a 2,2-dimethyl-3-acetyl-5-oxo-4-(substituted)-imidazolidin-1-yl group, and the 4-substituent (R') in the imidazolidinyl formula typically includes 1,4-cyclohexadienyl, phenyl, 3-bromophenyl, 2-chlorophenyl, 4-fluorophenyl, 3-iodophenyl, 3-chloro-4-fluorophenyl, 2-chloro-4-bromophenyl, 4-hydroxyphenyl, 4-formyloxyphenyl, 3-formyloxyphenyl, 4-nitrophenyl, 2-cyanophenyl, 3-trifluoromethylphenyl, 4-methylphenyl, 3-ethylphenyl, 4-isopropylphenyl, 4-t-butylphenyl, 3-methoxyphenyl, 2-ethoxyphenyl, 4-n-propoxyphenyl, 3-isopropoxyphenyl, 4-isobutoxyphenyl, and the like.

The process of this invention may conveniently be considered as a sequence involving two steps. First, the 3-hydroxymethylcephalosporin acid starting material is converted to its 3-oxy-substituted intermediate, the structure of which depends upon the particular reagent which is employed. Secondly, the thus-produced intermediate is separated from excess reagent and is treated with methanol to effect replacement of the oxy substitution, thereby to produce the desired 3-methoxymethylcephalosporin acid.

The first step of the process of this invention, that is, preparation of the intermediate, is accomplished by reacting the 3-hydroxymethylcephalosporin acid with one of the activating agents selected from the group consisting of trifluoroacetic anhydride, phosphorus trichloride, phosphorus oxychloride, and thionyl chloride. Although it is not intended that the following discussion in any way limit this invention, it is believed that the reaction which occurs in the first step of the process of this invention produces a conversion at two moieties of the cephalosporin starting material. The structure which it is believed is produced is as follows:

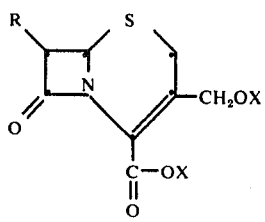

in which X in the above formula is dependent upon the particular reagent which is employed. X thus can be any of the following:

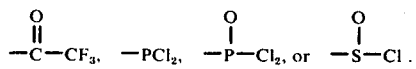

It will be noted, in order to produce the above-described intermediate, that it will be necessary to employ at least two moles of the activating agent per each mole of the cephalosporin starting material; however, it has been discovered that it is highly desirable to employ an even larger excess of the activating agent in order to accomplish sufficient preparation of the intended intermediate. Therefore, it is highly preferred to employ at least a 4:1 molar ratio of the activating agent to the cephalosporin starting material. Any amount in excess of this minimum can be present without detriment. Therefore, except by reason of the economics involved, there is no limitation to the maximum amount of the activating agent which can be employed.

The appropriate quantities of these reactants typically are dissolved in a suitable solvent, and the reaction is permitted to proceed. A suitable solvent typically is an inert polar organic solvent. By "inert" is meant a solvent which is compatible with the reactants which are employed and which does not enter into or modify the ongoing of the reaction involved. Typical such solvents include nitriles, such as acetonitrile, propionitrile, and the like; halogenated hydrocarbons such as methyl chloride, methylene chloride, chloroform, and the like; ethers such as tetrahydrofuran, ethyl ether, and the like; ketones, such as acetone, methyl ethyl ketone, and the like; esters, such as ethyl acetate, and the like; and such other suitable organic solvents. Preferably, the solvent which is employed should be moderately polar. Any of those described hereinabove are polar and therefore would be preferred. Also, the solvent should be relatively volatile. The purpose of this provision will be evident from the discussion which follows. By "relatively volatile" is meant a solvent which exhibits characteristics which permit its ready removal from the resulting reaction mixture by warming the mixture under vacuum conditions at a temperature not in excess of about 50° C. Each of the above-described solvents also readily meets this provision.

Furthermore, a mixture of any of the above-described solvents can be employed. In addition, it is possible, and, indeed, it is preferred to employ an aromatic hydrocarbon, such as toluene, xylene, and the like, in combination with one of the aforedescribed solvents. For example, it is highly preferred to employ acetonitrile as the solvent in the preparation of the intermediate as aforedescribed. It is even more preferred to employ, in addition to the acetonitrile solvent, a substantial quantity of toluene such that the resulting mixture of toluene and acetonitrile ranges by volume from about 3:1 to about 1:3.

The preparation of the intermediate is accomplished quite rapidly, the reaction generally being completed after about 30 minutes. Typically, the time of reaction is from about 5 to about 30 minutes. The preparation of the intermediate in general should be carried out at a relatively low temperature, generally from about −30° to about +20° C. Preferably, the temperature of reaction is from about −10° to about 0° C.

As mentioned hereinbefore, once the reaction of the 3-hydroxymethylcephalosporin acid and the activating agent is complete, the reaction mixture, containing an excess of the activating agent, is treated under conditions which will effect removal of substantially all of the excess activating agent and solvent which is employed, and, at the same time, will avoid decomposition of the prepared intermediate. These conditions involve evaporation of the excess activating agent and solvent at reduced pressure and with moderate warming such that the reaction mixture reaches a temperature no higher than about 50° C.

Once the excess activating agent and solvent are substantially removed, the resulting residue then is in condition for treatment in accordance with the second step of the process of this invention. In essence, this step involves reaction of the intermediate with methanol to produce the desired 3-methoxymethylcephalosporin acid. In fact, therefore, nothing more than these two reagents are required. The methanol itself can serve as solvent for the reaction medium. Whether or not a separate solvent is employed, a large excess of the methanol preferably also is employed. Generally, the ratio by weight of the methanol to the cephalosporin intermediate is at least about 10:1. The presence of a much larger quantity of methanol relative to the cephalosporin intermediate can be employed without detriment.

As noted above, a separate solvent can be employed. Primarily, this solvent is for the intermediate, and is for the purpose of ready addition of the cephalosporin intermediate to the methanol reactant. Such solvent should be anhydrous and should exhibit polar characteristics. Typical such solvents include nitromethane, acetonitrile, nitrobenzene acetone, methylene chloride, and the like. Preferably, the solvent of choice is acetonitrile or acetone, and more preferably, the solvent which is employed is acetonitrile. Should a solvent be employed, the cephalosporin intermediate recovered from the preceding step can be dissolved in the solvent in an amount which represents a highly concentrated mixture, the purpose of the solvent being to ensure complete transfer to the methanol reaction environment of the cephalosporin intermediate and its rapid dispersion therein.

The cephalosporin intermediate and methanol are reacted at a temperature of from about 45° to about 75° C. Preferably, the temperature of reaction will be that attained by reflux of the reaction mixture. Generally, the reaction temperature will range from about 65° to about 75° C. The reaction customarily is complete after a short period of time, normally from about 15 to about 90 minutes.

In carrying out the second step of the process of this invention, it is highly preferred to add the cephalosporin intermediate concentrate dissolved in a suitable solvent to the methanol maintained at the temperature of reaction, usually at reflux. Usually a dropwise addition is employed, and, when this method is carried out, the reaction generally is complete after the mixture has been maintained at the temperature of reaction for about 15 to 20 minutes after all of the cephalosporin intermediate is added.

It has been discovered that it is highly advantageous in this second step of the process of this invention to include an anhydrous alkali metal iodide in the methanol. Typical such alkali metal iodides include sodium iodide, potassium iodide, and lithium iodide. Preferably, sodium iodide is employed. When an iodide salt is employed, it should be present in the methanol in an amount at least equivalent to the amount of the cephalosporin intermediate which is to be reacted with the methanol. No detriment results from using an amount of the alkali metal iodide in excess of the equivalent amount; indeed, the iodide salt can be present in an amount up to and including that represented by a saturated solution of the iodide salt in the methanol. When an anhydrous alkali metal iodide is employed, the reaction is carried out in a manner such as is described hereinabove, the only exception being that the methanol which is heated and to which the cephalosporin intermediate is introduced by drop-wise addition comprises a solution of the iodide salt in the methanol. The use of an iodide salt as here described appears to avoid production of an undesired by-product, namely, the corresponding 3-exomethylene-4-methoxycephalosporin having the following structure:

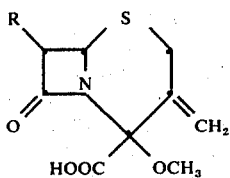

As noted hereinabove, the 3-hydroxymethylcephalosporin acid which is employed as starting material in the process of this invention can contain any of a wide variety of substituents in the 7-position. The identity of the substituent in the 7-position of the starting material can be suitably selected to be the particular substituent intended ultimately to be present in the final product which is obtained from the process of this invention. Alternatively, the particular substituent can be any of a wide variety of other such substituents. Employing readily recognized reaction techniques, any substituent which is present in the 7-position can be cleaved from the product obtained from the process of this invention to produce 7-amino-3-methoxymethyl-3-cephem-4-carboxylic acid. This then can be acylated, again by readily recognized techniques, to produce the desired 3-methoxymethylcephalosporin acid antibiotic. Thus, as is pointed out hereinabove, it matters not what the particular substituent in the 7-position of the cephalosporin starting material is since this can subsequently be modified to incorporate whatever particular substituent one wishes to have in the 7-position.

A sequence of a typical preparation of 7-amino-3-methoxymethyl-3-cephem-4-carboxylic acid from 7-aminodesacetylcephalosporanic acid (desacetyl 7-ACA) is as follows.

7-Amino-3-hydroxymethyl-3-cephem-4-carboxylic acid (desacetyl 7-ACA) (34.5 g.; 150 mmole) is suspended in 1 liter of a 1:1 mixture of water and acetone in a 4 liter beaker. The beaker is maintained in an ice bath. Approximately 50 percent of a solution of 31 g. (310 mmole) of potassium bicarbonate in 150 ml. of water is added from a dropping funnel to dissolve the cephalosporin starting material by raising the pH to 8.5–9.0. A solution of 34.5 g. (160 mmole) of p-nitrobenzyl chloroformate in 150 ml. of dry acetone then is added slowly from a dropping funnel over a period of 60 minutes. During addition, the pH of the reaction mixture is maintained from about 7 to about 8 by simultaneous drop-wise addition of the remainder of the potassium bicarbonate solution. The reaction mixture is stirred with cooling for an additional 60 minutes after completion of the addition of the p-nitrobenzyl chloroformate, the pH being maintained at about 7. The reaction mixture then is extracted three times by decantation with about 1200 ml. of ether. The decanted ether layers are washed with about 150 ml. of cold, dilute potassium bicarbonate solution, and the potassium bicarbonate solution is added to the aqueous layer. The aqueous layer then is covered with 1500 ml. of ethyl acetate containing about 10 percent ethanol. The resulting mixture is carefully, but quickly, acidified to pH 2.0 by addition of 6N hydrochloric acid. Cooling is maintained throughout. The ethyl acetate layer then is decanted, and the aqueous layer is washed several times with ethyl acetate. A precipitate may form at this point, making separation of the layers difficult or slow. In the event that this occurs, the mixture can be filtered through several thicknesses of filter paper with advantageous use of filter aide. Once obtained, the ethyl acetate layers are combined, dried over sodium sulfate, filtered, and concentrated in vacuo making certain that the mixture is not heated to an excessive temperature. Crystallization of the desired product, the ethyl acetate solvate of 7-(4-nitrobenzyloxycarbamido)-3-hydroxymethyl-3-cephem-4-carboxylic acid, generally occurs when the solvent volume reaches a suitable concentration, generally about 200–400 ml. Crystallization can be assisted by the addition of a small amount of acetone to the mixture. A second and sometimes a third crop of the product can be obtained by further concentration of the mother liquor.

The product which is obtained, a starting material in the process of this invention, then is placed in a round bottom flask and cooled in an ice bath. The mixture is suspended by stirring in a 2:1 mixture of dry toluene and dry acetonitrile. When the mixture has been sufficiently cooled, an excess of trifluoroacetic anhydride is added, and the mixture is stirred in the cold until all of the starting material has dissolved, which indicated formation of the desired trifluoroacetate intermediate.

Separately and concurrently, a three-neck, round bottom flask is equipped with a heating mantle, reflux condenser, stirrer, and a pressure equalizing dropping funnel. A flow of dry nitrogen is introduced at the top of the dropping funnel and is allowed to escape through the reflux condenser. To the flask is added 900 ml. of dry methanol, 50 ml. of trimethyl orthoformate, and 150 g. of anhydrous potassium iodide. The trimethyl orthoformate is added to assist in removing any residual amounts of water which may be in the reaction system. The mixture is heated to a gentle reflux.

In the trifluoroacetic anhydride reaction described above, about 15 minutes after completion of addition of the trifluoroacetic anhydride and starting material generally has dissolved, indicating completion of the reaction. The reaction mixture then is concentrated in vacuo to about one-forth volume (about 75–100 ml.). The resulting syrupy material is transferred to the dropping funnel used in the methanolysis reaction. Transfer is made employing up to an equal volume of dry acetonitrile in several small washes. Potassium hydrogen phosphate (24.1 g.; 150 mmole) then is added to the stirring, refluxing methanol mixture to serve as a pH buffer. An additional 100 ml. of dry methanol is employed to ensure addition of the potassium hydrogen phosphate. The cephalosporin intermediate concentrate in acetonitrile then is added dropwise to the refluxing methanol over a period of from about 45 to about 60 minutes. A flow of nitrogen is maintained through the dropping funnel to keep any methanol from entering the funnel. Upon completion of addition of the cephalosporin intermediate concentrate, the reaction mixture is heated for an additional 15 minutes. Approximately 75 percent of the solvent then is removed by distillation in vacuo, precaution being taken not to overheat the contents of the reaction mixture. The resulting residue then is transferred to a separatory funnel containing 1200 ml. of ethyl acetate and 600 ml. of ice cold dilute sodium bicarbonate solution. Heptane can be added at this point to facilitate clearance of any emulsion which may form. The resulting aqueous layer then is separated and washed twice with ethyl acetate. The resulting three ethyl acetate layers then are extracted with ice cold dilute sodium bicarbonate solution. If an emulsion forms, it can be cleared by addition of ethanol. The resulting ethyl acetate layers contain any undesired neutral lactone by-product which may have formed. The aqueous sodium bicarbonate layers contain the desired 3-methoxymethylcephalosporin acid in the form of its sodium salt. The desired product can be recovered by combining the aqueous layers in a large vessel, covering the aqueous composite with ethyl acetate, and acidifying the aqueous mixture to pH 1.5 by addition of 6N hydrochloric acid. The ethyl acetate layer then is separated, washed once with saturated sodium chloride solution, and dried over sodium sulfate. The aqueous layer then is extracted again with ethyl acetate and discarded. The ethyl acetate layers are combined, dried over sodium sulfate, filtered, and evaporated in vacuo to dryness. The resulting crude product is obtained as a foam which can be crystallized from acetone or ethanol to obtain the desired 7-(4-nitrobenzyloxycarbamido)-3-methoxymethyl-3-cephem-4-carboxylic acid in pure form.

The 7-substituent then can be cleaved to produce the corresponding 7-amino compound which then can be reacylated to produce any 3-methoxymethylcephalosporin acid which one may desire. The cleavage can be carried out as follows:

The above product (26.0 g.; 61.5 mmole) is dissolved in 92 ml. of dry N,N-dimethylformamide in a round bottom flask equipped with a thermometer, a stirrer, a heater, and a water bath. The water bath initially is at room temperature. Thiophenol (61 ml.; about 590 mmole) is added followed by about 12 g. of zinc dust added in small portions with stirring over about a 10 minute period. Extreme care is taken to limit the amount of zinc dust which is added until the initial exothermic reaction is over. An induction period of from about 1 to about 5 minutes before the exothermic reaction occurs is common. Upon completion of the initial exothermic reaction, the zinc dust can be added more rapidly; however, the temperature should not rise above about 65° C. Upon completion of the initial exothermic reaction, the water bath is heated, and the temperature of the reaction mixture is maintained at about 60°–65° C. for about 1 hour. Carbon dioxide evolution occurs with the formation of a precipitate. The reaction mixture then is cooled to about 0° C., and the precipitated product is dissolved by addition of sufficient concentrated hydrochloric acid to lower the pH to about 1.0–1.3. The resulting cold solution then is filtered to remove any zinc residue, and the product is reprecipitated by raising the pH to 3.8 by addition of concentrated ammonium hydroxide. This addition is done with ice bath cooling. After cooling the mixture for 1–2 hours, the product is removed by filtration and washed with ethanol and/or methanol to remove any excess N,N-dimethylformamide and thiophenol. The product then is dried in vacuo to obtain 7-amino-3-methoxymethyl-3-cephem-4-carboxylic acid.

The resulting product then can be acylated using known techniques to obtain any of a wide variety of 3-methoxymethylcephalosporin antibiotics. The methods used to obtain these antibiotically active compounds are well recognized in the art.

In further elaboration of the invention of this application, the following examples are provided. The examples are illustrative of the process of this invention. They by no means are intended to be limiting upon the scope thereof.

EXAMPLE 1

To a mixture of 4 ml. of dry acetonitrile and 8 ml. of dry toluene were added 1.968 g. (4.0 mmole) of 7-(4-nitrobenzyloxycarbonylamino)-3-hydroxymethyl-3-cephem-4-carboxylic acid. The resulting mixture was cooled in an ice bath. Trifluoroacetic anhydride (1.2 ml.) was added to the suspension of the cephalosporin in the acetonitriletoluene mixture. After a few minutes, the suspended 3-hydroxymethylcephalosporin acid dissolved, and the solution was complete. The mixture then was evaporated to dryness on a rotary evaporator. A foam resulted which was dissolved in dry acetonitrile. The acetonitrile solution then was added dropwise to a refluxing mixture of 36 ml. of methanol, 2 ml. of trimethyl orthoformate, 6 g. of potassium iodide, and 1 g. of potassium hydrogen phosphate. The dropwise addition extended over a 20 minute period after which the resulting mixture was refluxed for an additional 15 minutes. The mixture then was evaporated in vacuo to approximately one-third its original volume. The concentrated reaction mixture then was worked up in the manner described hereinbefore to obtain 939 mg. (55.6 percent) of the desired 7-(4-nitrobenzyloxycarbonylamino)-3-methoxymethyl-3-cephem-4-carboxylic acid. In addition, there was recovered as a neutral fraction 922 mg. of the corresponding lactone by-product.

EXAMPLE 2

To a mixture of 15 ml. of acetonitrile and 15 ml. toluene were added 3.78 grams (8.16 mmoles) of 7-(α-t-butoxycarbonylamino)-phenylacetamido-3-hydroxymethyl-3-cephem-4-carboxylic acid. The mixture was cooled to an ice bath, and 3.2 ml. of trifluoracetic anhydride were added. Solution was complete after 10–15 minutes. The solution was concentrated in vacuo to a small volume, and the residual gum was taken up in dry acetonitrile. The resulting solution then was added dropwise over a 15 minute period to a refluxing mixture of 80 ml. of dry methanol, 4 ml. of trimethyl orthoformate, 40 grams of sodium iodide, and 5.57 grams of potassium hydrogen phosphate. The mixture was refluxed for an additional 20 minutes after which the principal portion of the solvent was removed in vacuo. The residue then was taken up in a mixture of ice cold dilute sodium bicarbonate solution and ethyl acetate. The mixture then was worked up in a manner described hereinbefore to obtain 2.65 gms. of crude acidic material and 1.76 gms. of a neutral fraction of the corresponding lactone by-product. NMR analysis of the acidic material indicated that approximately 50 percent of the material represented the desired 7-($\alpha$-t-butoxycarbonylamino)phenylacetamido-3-methoxymethyl-3-cephem-4-carboxylic acid.

I claim:
1. A process for preparing a 3-methoxymethylcephalosporin of the formula

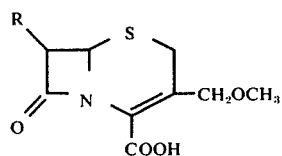

which comprises contacting a 3-hydroxymethylcephalosporin of the formula

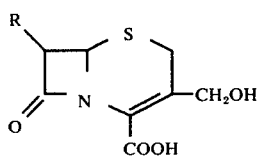

with at least four equivalents of an activating agent selected from the group consisting of trifluoracetic anhydride, phosphorus trichloride, phosphorus oxychloride, and thionyl chloride at a temperature of from about −30° to about +20° C. to produce an intermediate compound, separating the resulting intermediate from excess activating agent by treating the reaction mixture at reduced pressure and at a temperature not in excess of about 50° C., and reacting said intermediate with an excess of methanol at a temperature of from about 45° to about 75° C. to produce the aforementioned product, in any of the above in which R is 1. an imido group of the formula

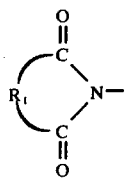

in which $R_1$ is $C_2$-$C_4$ alkylene or 1,2-phenylene;
2. an amido group of the formula

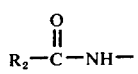

in which $R_2$ is a. hydrogen, $C_1$-$C_3$ alkyl, halomethyl, 4-amino-4-carboxybutyl, 4-protected amino-4-protected carboxybutyl, benzyloxy, 4-nitrobenzyloxy, t-butyloxy, 2,2,2-trichloroethoxy, 4-methoxybenzyloxy, 3-(2-chlorophenyl)-5-methylisoxazol-4-yl;
b. the group R' in which R' is 1,4-cyclohexadienyl, phenyl, or phenyl substituted with one or two halogens, hydroxy, protected hydroxy, nitro, cyano, trifluoromethyl, $C_1$-$C_4$ alkyl, or $C_1$-$C_4$ alkoxy;
c. a group of the formula R'—(O)$_m$—CH$_2$— in which R' is as defined above and m is 0 or 1;
d. a group of the formula

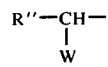

in which R'' is R' as defined above, 2-thienyl, or 3-thienyl, and W is hydroxy, protected hydroxy, carboxy, protected carboxy, amino, or protected amino;
e. a group of the formula '''—CH$_2$— in which R''' is 2-thienyl, 3-thienyl, 2-furyl, 3-furyl, 2-thiazolyl, 5-tetrazolyl, 1-tetrazolyl, or 4-isoxazolyl; or R is
3. an imidazolidinyl group of the formula

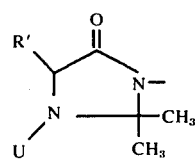

in which R' is as defined above and U is nitroso or acetyl.
2. Process of claim 1, in which R is

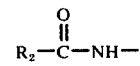

and $R_2$ is hydrogen, methyl 4-nitrobenzyloxy, benzyl, phenoxymethyl, thien-2-ylmethyl, tetrazol-1-ylmethyl, or $\alpha$-(t-butyloxycarbonylamino)benzyl.
3. Process of claim 1, in which the activating agent is trifluoroacetic anhydride.
4. Process of claim 3, in which the reaction of the 3-hydroxymethylcephalosporin and the activating agent is carried out in the presence of an inert polar organic solvent.
5. Process of claim 4, in which the inert polar organic solvent is acetonitrile and is present as a mixture of acetonitrile and toluene ranging from about 3:1 to about 1:3 by volume.
6. Process of claim 3, in which the ratio by weight of the methanol of the intermediate is at least about 10:1.
7. Process of claim 3, in which an anhydrous alkali metal iodide is included in the reaction mixture during reaction of the intermediate with methanol.
8. Process of claim 7, in which the anhydrous alkali metal iodide is present in an amount at least equivalent to the amount of intermediate which is present.
9. Process of claim 8, in which the anhydrous alkali metal iodide is sodium iodide.

* * * * *

UNITED STATES PATENT AND TRADEMARK OFFICE
CERTIFICATE OF CORRECTION

PATENT NO. : 4,008,231
DATED : Feb. 15, 1977
INVENTOR(S) : Ian G. Wright

It is certified that error appears in the above-identified patent and that said Letters Patent are hereby corrected as shown below:

Column 14, line 22, "e. a group of the formula''' " should read --e. a group of the formula R'''--.

Signed and Sealed this

Twenty-eighth Day of June 1977

[SEAL]

Attest:

RUTH C. MASON
*Attesting Officer*

C. MARSHALL DANN
*Commissioner of Patents and Trademarks*